(12) United States Patent
Magnenat et al.

(10) Patent No.: US 9,833,565 B2
(45) Date of Patent: Dec. 5, 2017

(54) PATCH AND INFUSION SET ASSEMBLY

(71) Applicant: DEBIOTECH S.A., Lausanne (CH)

(72) Inventors: Olivier Magnenat, Lausanne (CH); Frédéric Neftel, Lausanne (CH)

(73) Assignee: DEBIOTECH S.A., Lausanne (CH)

( * ) Notice: Subject to any disclaimer, the term of this patent is extended or adjusted under 35 U.S.C. 154(b) by 0 days.

(21) Appl. No.: 14/357,327

(22) PCT Filed: Nov. 2, 2012

(86) PCT No.: PCT/IB2012/056113
§ 371 (c)(1),
(2) Date: May 9, 2014

(87) PCT Pub. No.: WO2013/068900
PCT Pub. Date: May 16, 2013

(65) Prior Publication Data
US 2014/0316378 A1 Oct. 23, 2014

(30) Foreign Application Priority Data
Nov. 10, 2011 (EP) ..................................... 11188705

(51) Int. Cl.
*A61M 5/142* (2006.01)
*A61M 5/158* (2006.01)

(52) U.S. Cl.
CPC ........ *A61M 5/14248* (2013.01); *A61M 5/158* (2013.01); *A61M 2005/14252* (2013.01)

(58) Field of Classification Search
CPC ...... A61M 5/14248; A61M 2005/1585; A61M 2005/1586; A61M 2005/1587; A61M 2005/14252; A61M 25/0637; A61M 2025/024; A61M 2209/088
See application file for complete search history.

(56) References Cited

U.S. PATENT DOCUMENTS

| 2,605,765 | A | * | 8/1952 | Kollsman | ......... | A61M 5/14248 |
| | | | | | | 604/135 |
| 2003/0176852 | A1 | * | 9/2003 | Lynch | ............... | A61M 5/14244 |
| | | | | | | 604/890.1 |
| 2005/0101932 | A1 | | 5/2005 | Cote et al. | | |

(Continued)

FOREIGN PATENT DOCUMENTS

JP  2010-540095 A  12/2010
WO  WO 2007/141210  12/2007

(Continued)

OTHER PUBLICATIONS

International Search Report for PCT/IB2012/056113 dated Mar. 15, 2013.

(Continued)

*Primary Examiner* — Nathan R Price
*Assistant Examiner* — Justin L Zamory
(74) *Attorney, Agent, or Firm* — Nixon & Vanderhye P.C.

(57) ABSTRACT

The invention relates to an assembly that includes an infusion set and a patch intended for receiving a pump for the transcutaneous administration of a product, said patch including an adhesive portion and a non-adhesive portion, the assembly being characterized in that said set includes patch-guiding elements and sliding elements intended for sliding along the guiding elements.

18 Claims, 11 Drawing Sheets

(56) References Cited

U.S. PATENT DOCUMENTS

| | | | |
|---|---|---|---|
| 2005/0240154 A1 | 10/2005 | Mogensen et al. | |
| 2005/0273059 A1* | 12/2005 | Mernoe | A61M 5/14248 604/180 |
| 2006/0264835 A1* | 11/2006 | Nielsen | A61M 5/14248 604/174 |
| 2007/0149921 A1* | 6/2007 | Michels | A61M 5/158 604/93.01 |
| 2008/0228144 A1* | 9/2008 | Liniger | A61M 5/158 604/164.08 |
| 2008/0281270 A1 | 11/2008 | Cross et al. | |
| 2010/0049128 A1* | 2/2010 | McKenzie | A61M 5/14248 604/135 |
| 2010/0198157 A1* | 8/2010 | Gyrn | A61M 5/14248 604/151 |
| 2010/0234805 A1* | 9/2010 | Kaufmann | A61M 5/14248 604/151 |

FOREIGN PATENT DOCUMENTS

| | | | |
|---|---|---|---|
| WO | WO 2007/141210 A1 | 12/2007 | |
| WO | 2009/045780 A2 | 4/2009 | |

OTHER PUBLICATIONS

IPRP/Written Opinion and its English Translation for PCT/IB2012/056113, dated May 13, 2014.

\* cited by examiner

PATCH AND INFUSION SET ASSEMBLY

This application is the U.S. national phase of International Application No. PCT/IB2012/056113 filed 2 Nov. 2012 which designated the U.S. and claims priority to EP Patent Application No. 11188705.5 filed 10 Nov. 2011, the entire contents of each of which are hereby incorporated by reference.

FIELD OF THE INVENTION

The invention relates to the transcutaneous administration of a product by means of a pump mounted on a patch and connected to an infusion set.

More specifically, the invention relates to a set constituted of a patch and an infusion set.

PRIOR ART

Patch and infusion set assemblies are particularly disclosed in patent documents EP 1 970 091 A1 and US 2004/0158207.

The utilization of such assemblies enables a pump near the infusion set to be easily connected, disconnected and reconnected by eliminating the kind of tubing between the pump and the set.

Placement of the adaptation patch on the infusion set must be as easy as possible for the patient, but also must guarantee correct positioning in all cases.

As a general rule, the adhesive patch is first placed on the skin of the patient, and then a cannula or infusion set is inserted in the patch which serves as a fluid connection between the pump and the patient. This requires an inserter for the cannula, an inserter which must be adapted to the patch in order to place the cannula precisely before its insertion.

GENERAL DESCRIPTION OF THE INVENTION

The problems identified in the previous chapter may be resolved by the present invention, the object of which is described in the claims.

The present invention simplifies and improves the positioning of the patch and/or insertion device of the infusion set. The invention offers the possibility to the user of initially carrying out a step of inserting the infusion set without being bothered by the patch and placing the infusion set in the desired orientation. Said patch may be placed in a second step. Thus, a simplified and more economical inserter may be used for inserting the infusion set.

In the present invention, an infusion set is an element installed on a patient, comprising a cannula (or needle(s) or microneedle(s)), means for connecting to a solution administration or sample collection system and, preferentially, an adhesive to be fixedly stuck to the skin of the patient. Said infusion set enables a fluid path between said system and the patient to be created. Said connection means of the infusion set also comprise a septum to guarantee proper connection and sealing between the infusion set and said system. An inserter, automatic or manual, may be used for the installation of said infusion set. A patch is an element installed on a patient and at least partially comprising an adhesive to be stuck to said patient. Said patch enables said solution administration or sample collection system to be easily installed on said patient. Said solution administration or sample collection system may be a pump for the administration of a solution such as insulin. In this application, the terms "pump" and "solution administration system" will be used indifferently.

Each subassembly has one or more given functions, the infusion set ensures the fluid connection of the pump or collection system to the patient and the patch ensures the proper positioning and therefore the proper connection of the pump or collection system with the infusion set. It may also ensure, at least partially, the mechanical attachment of the pump or collection system to the skin of the patient.

The present invention also enables the patch to be positioned as precisely as possible after insertion of the infusion set. Thus, preferentially, the patient uses an inserter which facilitates insertion of the cannula (or needle(s) or microneedle(s)) of the infusion set into the patient. The infusion set (installed and temporarily stuck to the patient) may then be assembled with said patch that will also be temporarily stuck to said patient. Said infusion set and said patch thereby form an assembly intended to receive a pump or collection system, said assembly being composed of two portions to facilitate its installation. In addition, once the assembly is installed on the patient, said pump or said collection system may be easily connected to or disconnected from the assembly according to the needs and/or activities of the patient.

In another embodiment, the infusion set is manually inserted without using an inserter (automatic or not).

Locking of the patch and infusion set also guarantees, for each connection of the pump or collection system with the infusion set, that the needle of the pump is aligned with the septum of the set even if the site chosen by the patient is not absolutely flat.

Given that the assembly according to the invention guarantees optimal positioning of the patch with relation to the infusion set, a device for detecting the effective connection of the infusion pump or collection system to the set may be considered via detection of the connection of the pump or collection system to the patch. By way of example, the pump or collection system may detect (by a Hall effect detector) the presence of a magnet situated on the patch, thus indicating a correct connection to the infusion set. Due to the locking of the infusion set to the patch, a magnet placed either on the infusion set or on the patch will have the same function, knowing that it may be preferable to place said magnet on the patch.

The present invention particularly facilitates the placement of a patch and guarantees that it is correctly positioned.

Said patch also comprises a lower face disposing an adhesive portion and another non-adhesive portion in order to facilitate assembly with the infusion set and removal of said assembly.

The invention will be better understood below by means of a non-limiting embodiment illustrated by a few figures.

DETAILED DESCRIPTION OF THE INVENTION

Figure 5:
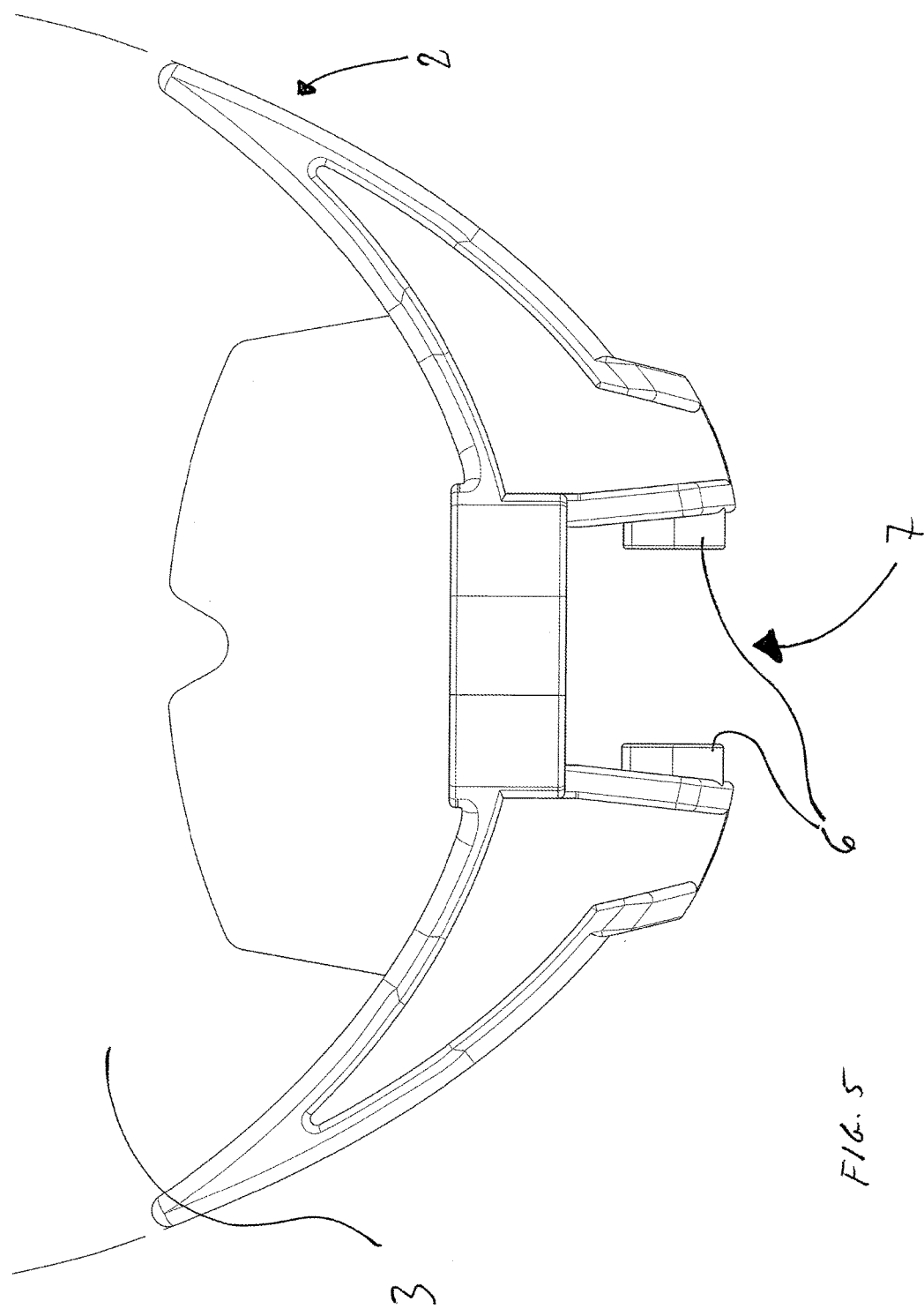

FIG. 5 presents the flared shape of a patch zone in which two lugs are disposed.

Figure 6:
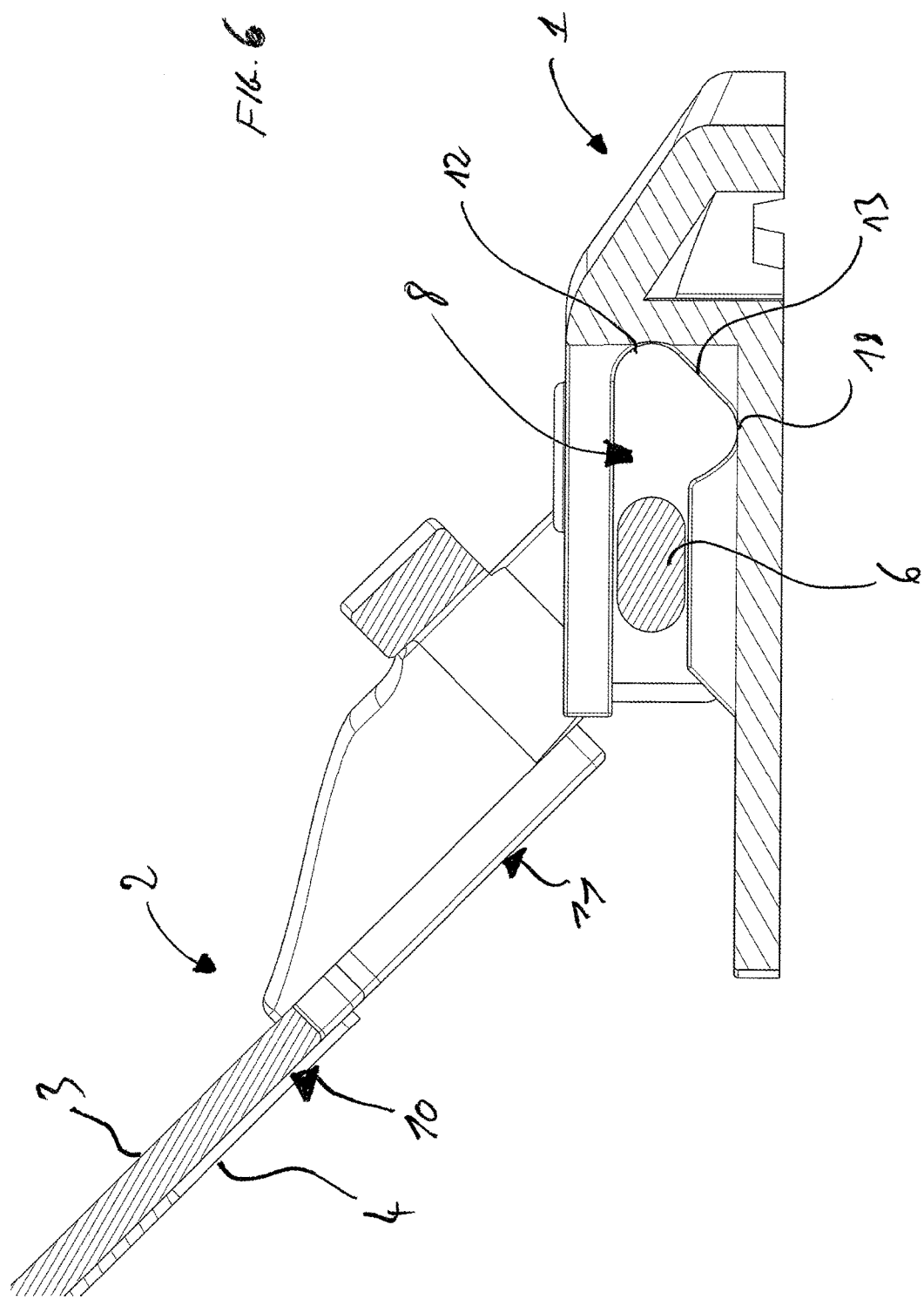

FIG. 6 illustrates a mechanism enabling an accidental pulling down of the patch against the skin to be prevented.

Figure 7:
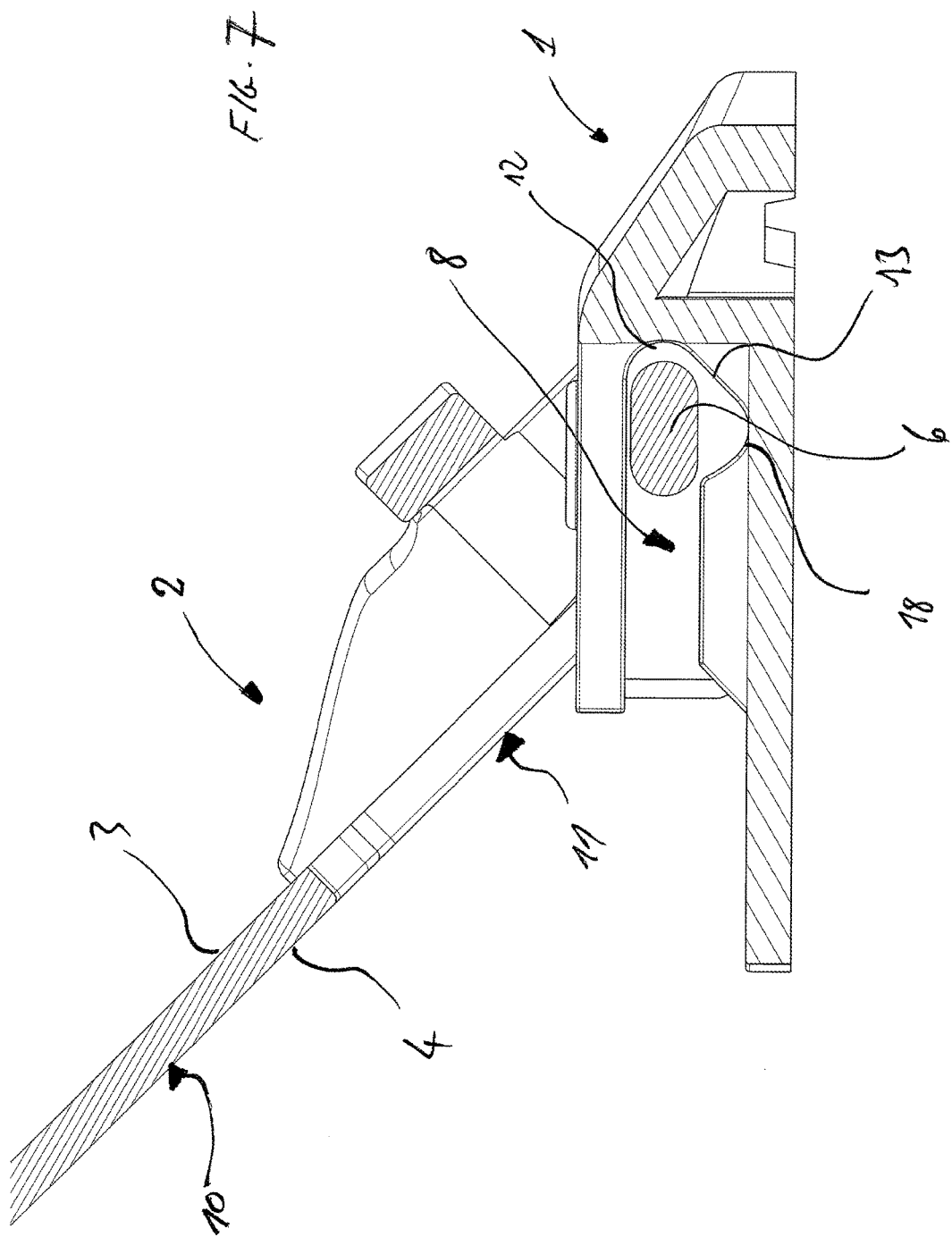

FIG. 7 shows the positioning of the patch that precedes its rotation to its final position.

Figure 8:
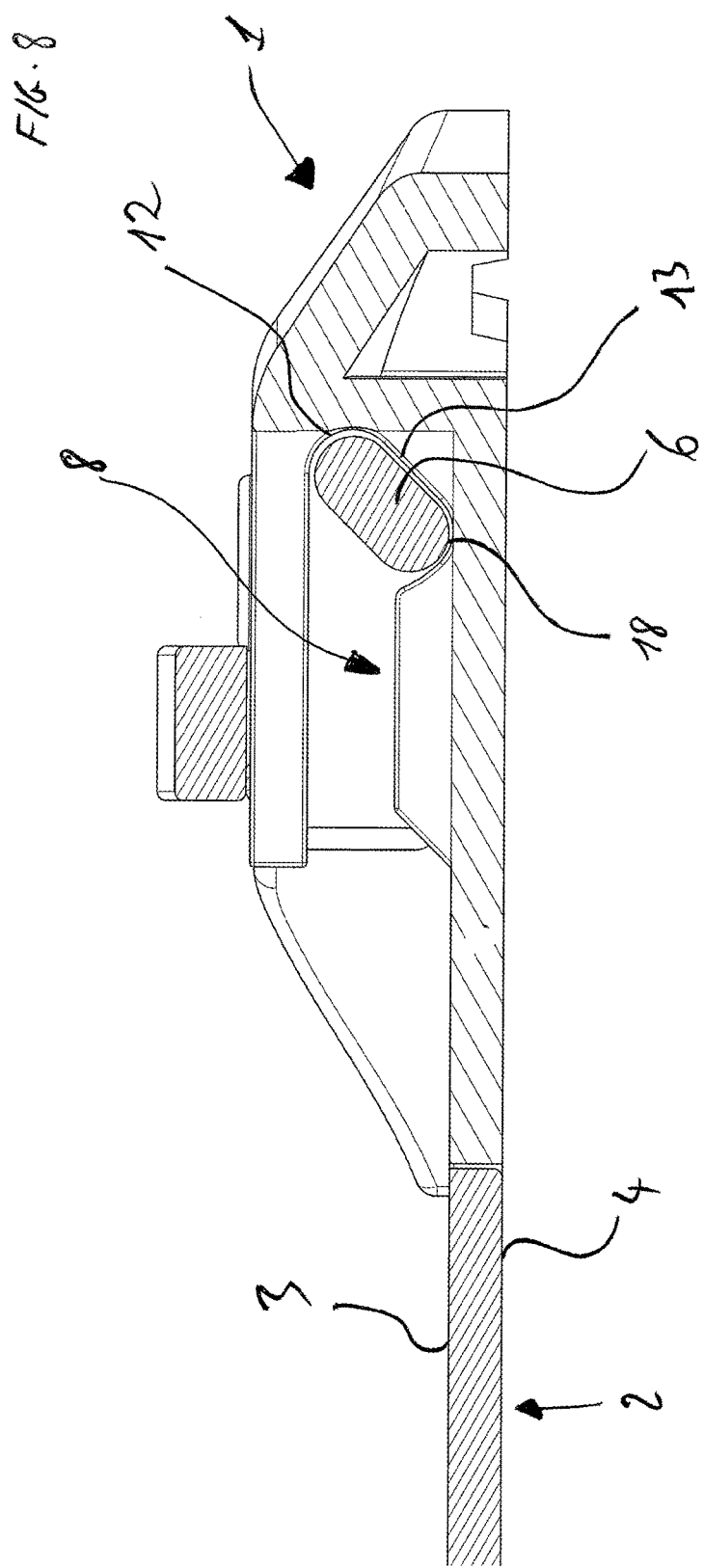

FIG. 8 presents the patch in its final position.

Figure 9:
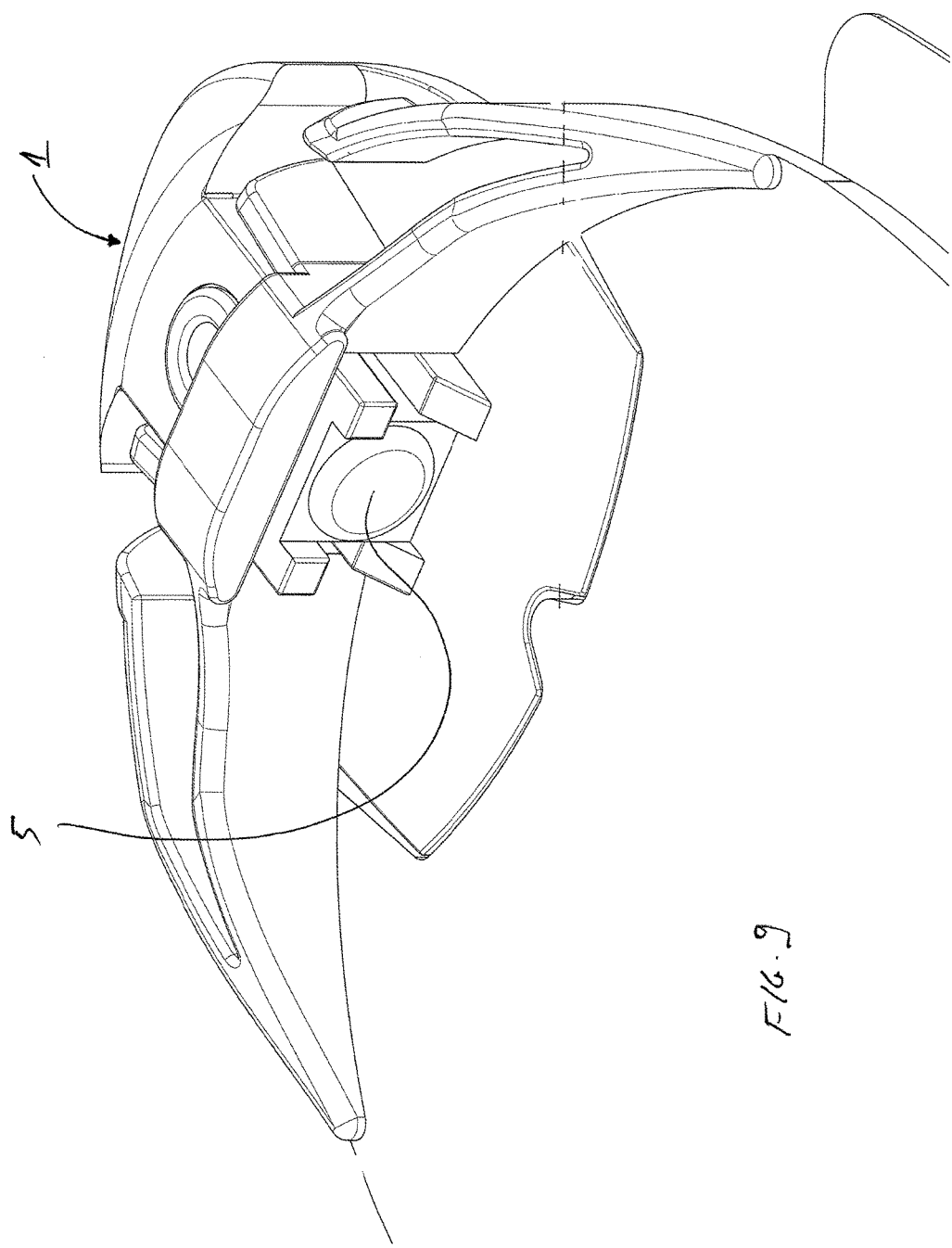

FIG. 9 presents the contact zone between the set and the patch.

Figure 10:
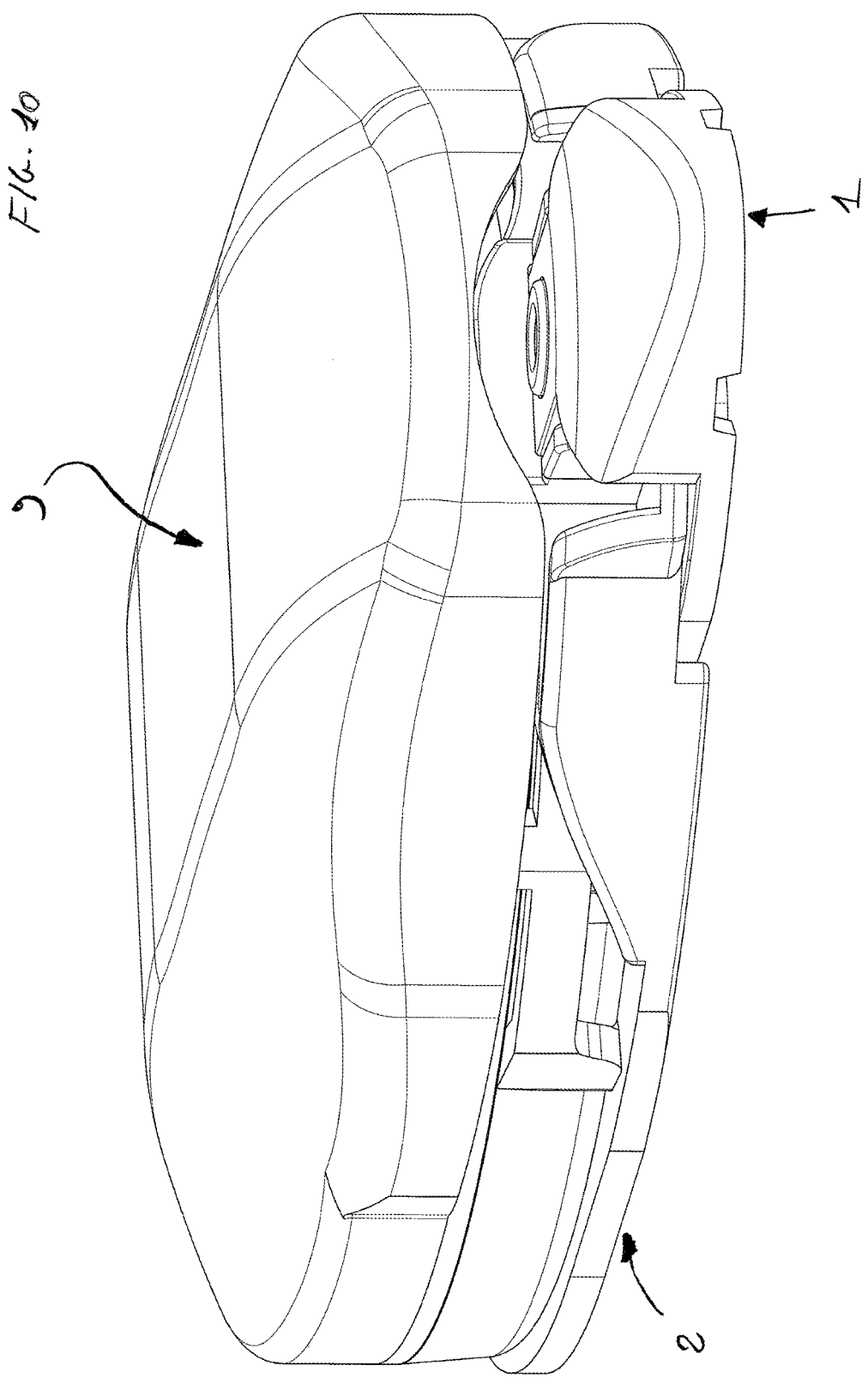

FIG. 10 represents the assembly according to the invention on which a pump is mounted.

Figure 11:
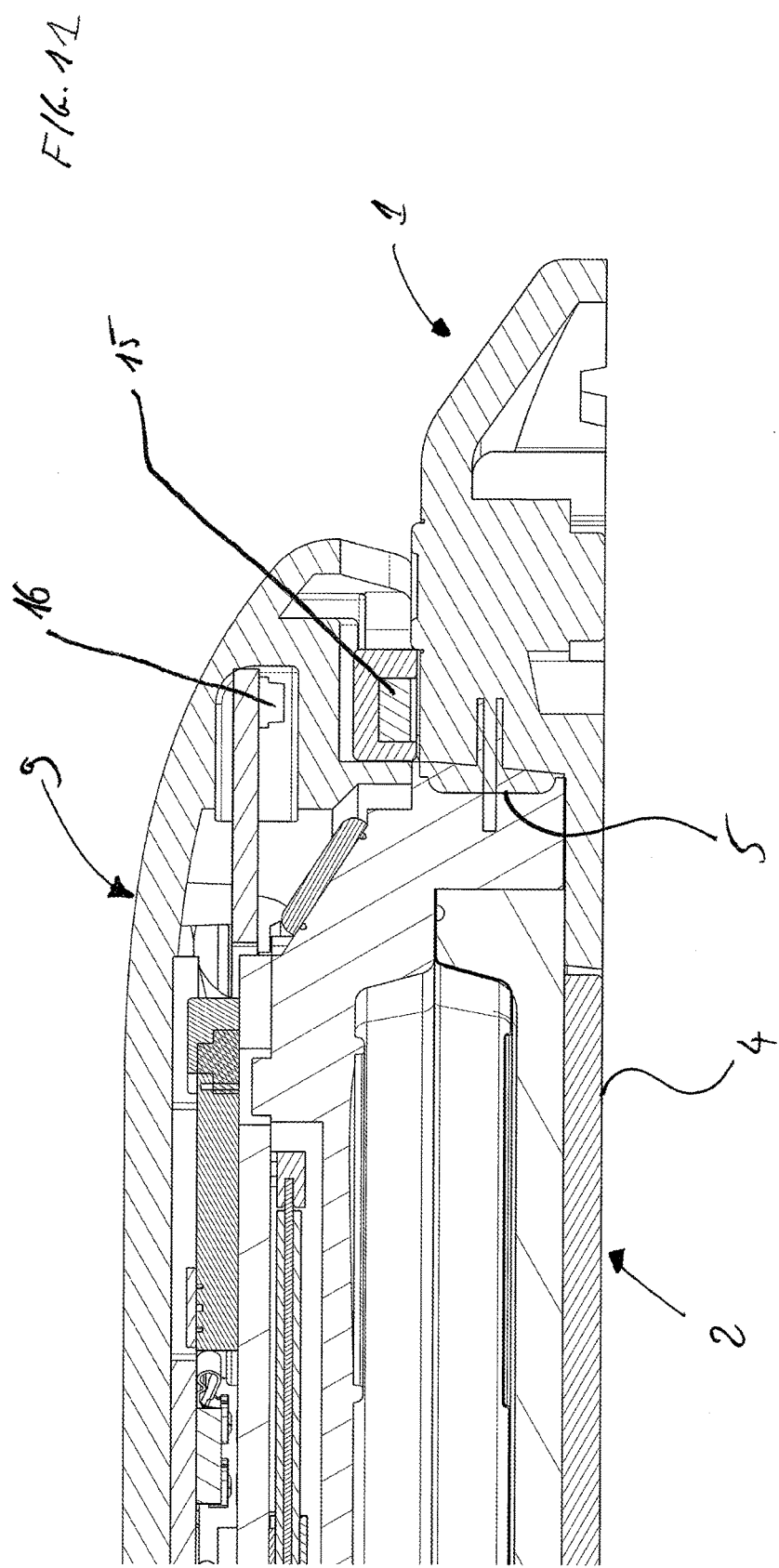

FIG. 11 illustrates a section of a portion of the object from FIG. 10.

NUMERICAL REFERENCES USED IN THE FIGURES

1. Infusion set
2. Patch
3. Upper face of the patch
4. Lower face of the patch
5. Septum
6. Lugs
7. Inter-lug space
8. Tracks
9. Pump
10. Adhesive portion
11. Non-adhesive portion
12. Stop
13. Ramp
14. Gripping zone
15. Magnet
16. Sensor
17. Passage
18. Recess In order to facilitate understanding of the invention, patch 2 particularly presented in FIG. 2 does not comprise means to ensure fixation of a pump 9.

Also to be noted is the absence of an illustration of the adhesive zone on the lower face 4 of patch 2. Before use, this adhesive zone is covered with a protective film.

Figure 1:
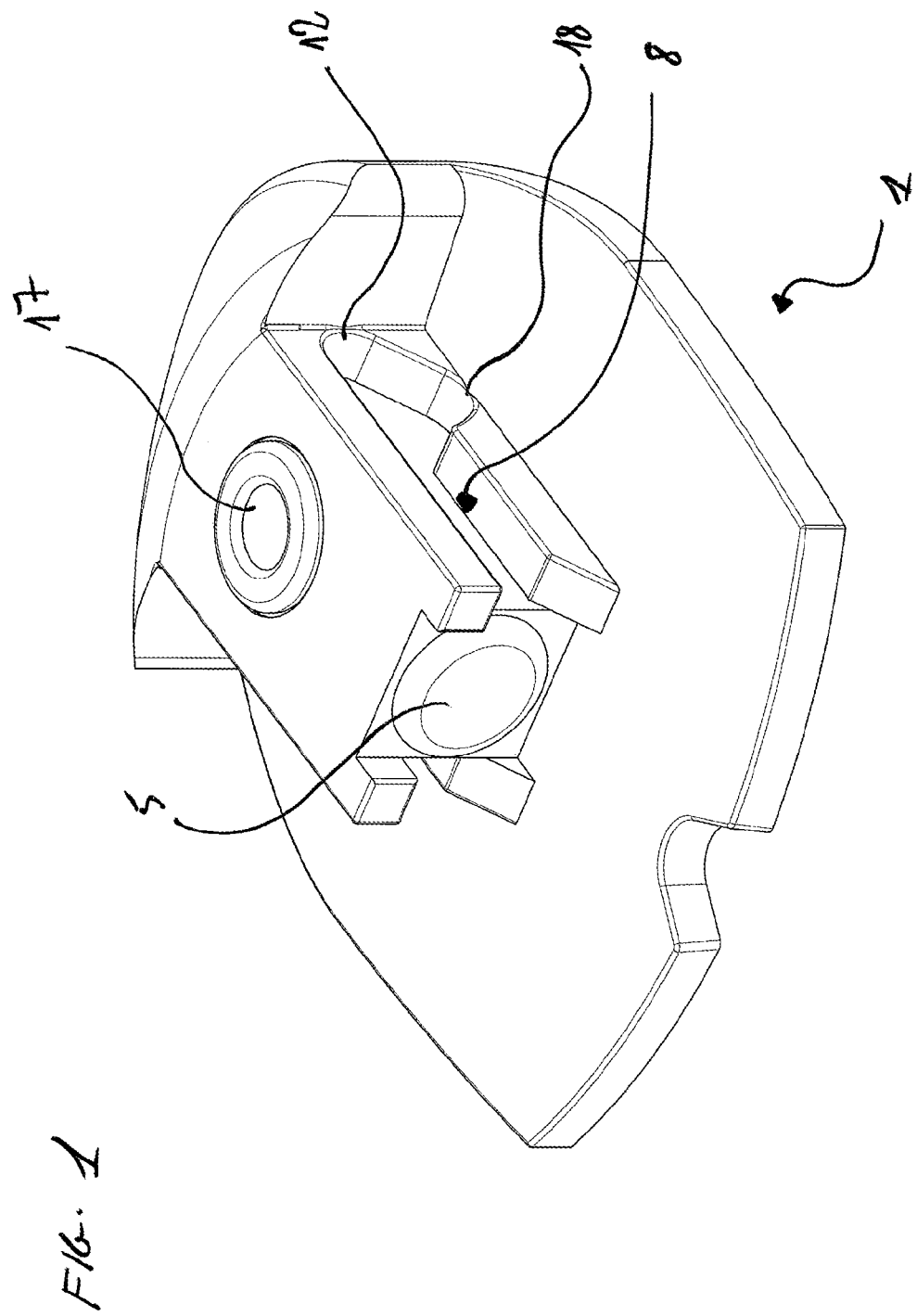
FIG. 1 represents an infusion set (without the cannula) according to the invention.

The infusion set 1 particularly illustrated in FIG. 1 comprises a septum 5 that closes a channel (not illustrated) ensuring fluid communication between a pump and a cannula. The infusion set 1 also comprises a passage for the introduction and removal of a mandrel. Preferentially, it lastly comprises patch-guiding elements that are presented in the form of tracks 8.

In a preferred embodiment (not illustrated), the infusion set comprises a base, the lower face of which comes into contact with the skin of the patient and the upper face may come into contact with a portion of the patch. The lower face of said infusion set may contain an adhesive on at least one portion of its surface in order to be fixedly held to the skin of the patient.

Figure 2:
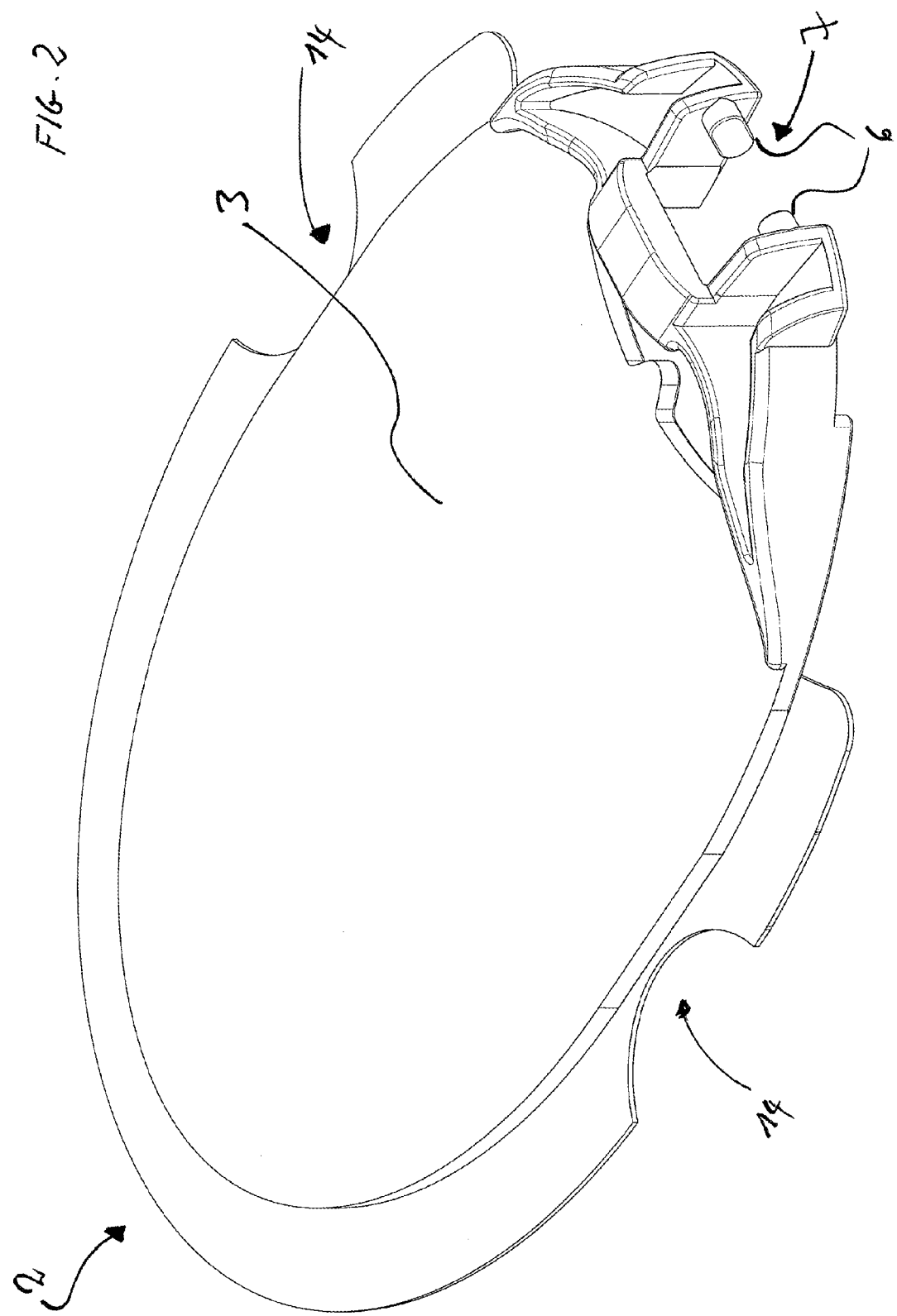
FIG. 2 represents a patch according to the invention that may be used with the set from FIG. 1.

FIG. 2 presents a patch 2 that is compatible with the infusion set 1 from FIG. 1. Said patch 2 comprises a base in which the lower face 4 is in contact with the skin and the upper face 3 is intended to receive a pump. Patch 2 comprises two removal zones 14 to facilitate gripping of the patch 2 with the fingers. The front portion of patch 2 comprises a flared zone 7 at the edge of which two lugs 6 are disposed, intended to slide in the tracks 8 of the infusion set 1.

Figure 3:
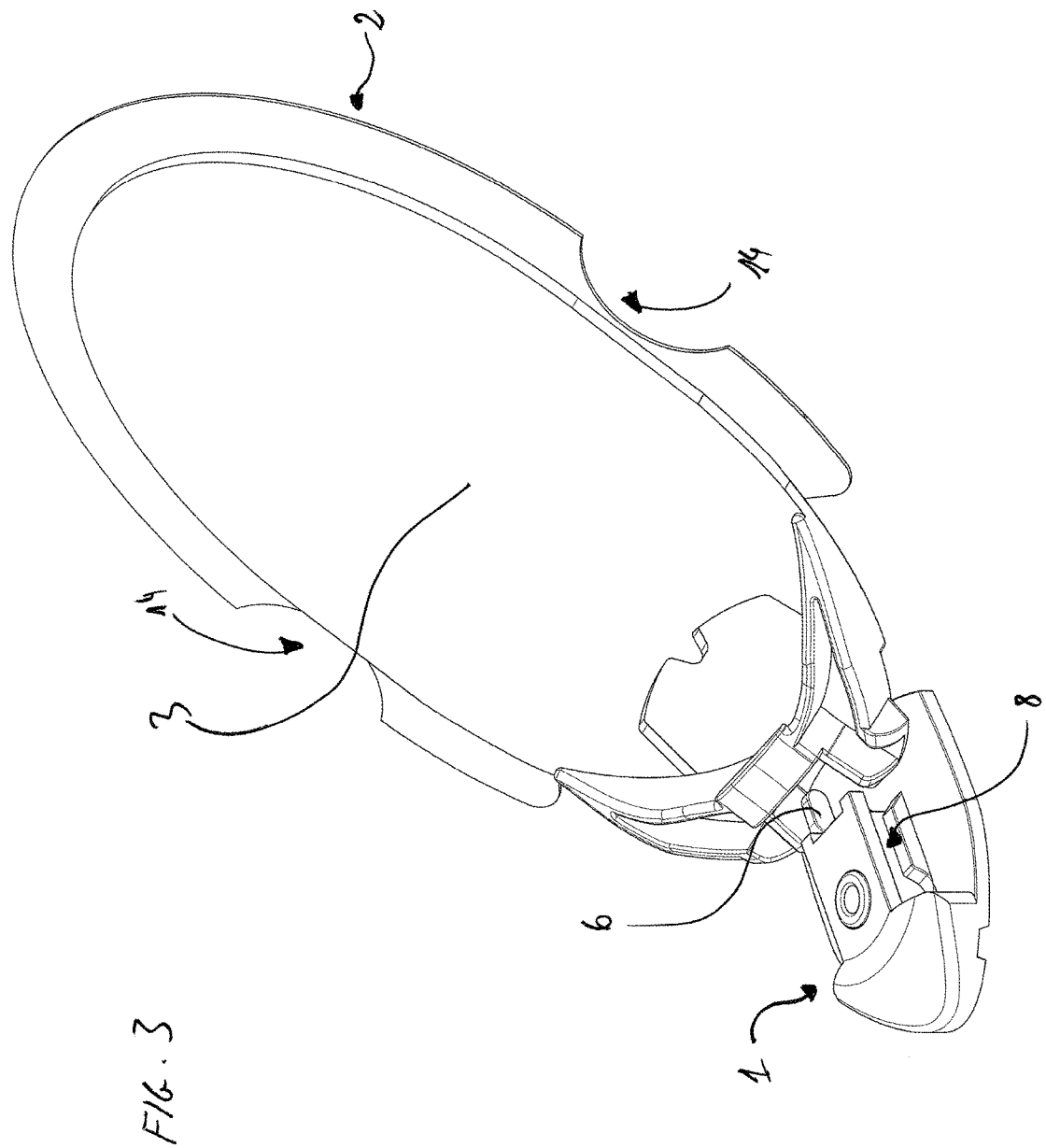
FIG. 3 illustrates the approach of the patch from FIG. 2 towards the set from FIG. 1.

Patch 2 comprises an adhesive 10 on at least one portion of the lower face 4 (FIG. 3) of said patch. A non-adhesive portion 11 of said patch 2 is located at the level where the infusion set 1 and the patch 2 are or may be in contact.

Preferentially, the base of said patch 2 is shaped so as to enable fitting of the base of said patch 2 and the base of said infusion set 1 and to create a continuous or semi-continuous flat part formed by the two bases to facilitate insertion of the pump by sliding on the patch 2 in the direction of the infusion set 1.

In another embodiment (not illustrated), the adhesive protrudes beyond the lower face of said patch 2. This embodiment produces less stress on the patch when it is installed on a non-compliant zone to the lower face 4 of said patch. It thus ensures proper maintenance since the entire adhesive zone is in contact with the skin. The patch may also have a reduced size or even a size smaller than the pump. This embodiment prevents the patient from being disturbed or experiencing discomfort caused when the patient is resting or moving.

Following removal of its protective film disposed on lower face 4 (see FIG. 3), the patch 2 approaches the infusion set 1 (already installed on the skin of the patient) while maintaining a certain angle with the surface of the skin. Ideally, such an angle is 30° to 60°, but preferably greater than 15°. The end of patch 2 engages the infusion set 1 and thus offers a first placement reference.

Patch 2 is maintained in contact with the infusion set 1 and may slide in the direction of septum 5. The flared shape of the front portion 7 of the patch 2 enables it to easily pass the septum portion 5 of the infusion set 1 in its center.

This same shape 7 (see FIG. 5) also enables the positioning of the patch 2 to be fine-tuned as it slides.

Figure 4:
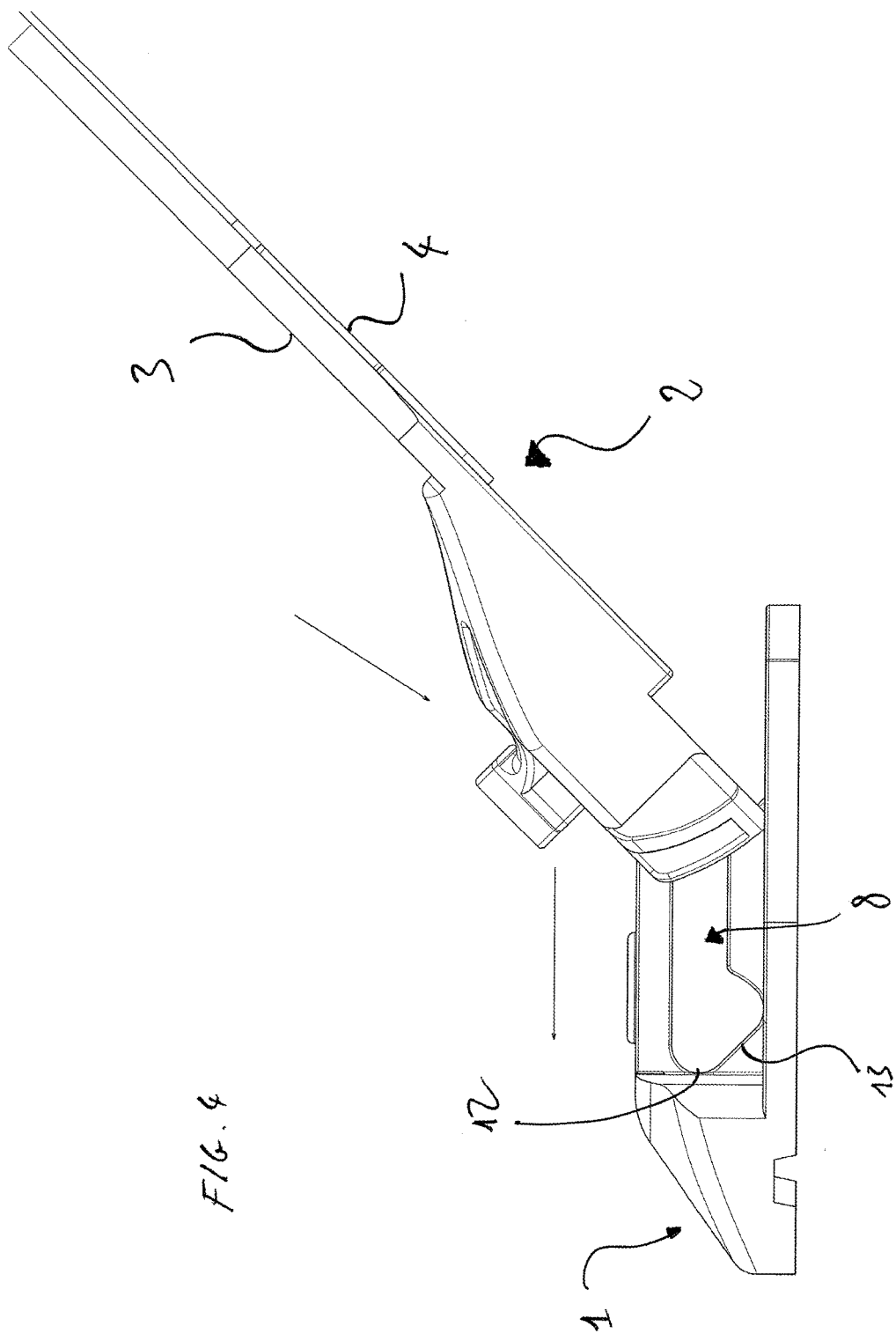
FIG. 4 shows the contact zone of the two portions and the direction of sliding of the patch.

Two lugs 6 disposed on patch 2 (see FIG. 4) will then slide between tracks 8 of set 1, in the direction of septum 5.

Either by a specific design for lugs 6 and/or tracks 8 or by any other system, it is preferable that patch 2 cannot be pulled down against the skin until it has reached its final position. In fact, a poorly positioned patch 2 may make the connection of a pump with the infusion set 1 impossible.

The assembly according to the invention as illustrated prevents this accidental pulling down of patch 2 when it is displaced to its final position.

As may be seen in particular in FIG. 6, once the lugs 6 are engaged in tracks 8, the patch 2 can only translate in the direction of tracks 8. As the lugs 6 are oriented along a direction oblique in relation to the main orientation of the patch 2, the latter can only be displaced by staying along a direction oblique in relation to the surface of the skin when it is displaced in the tracks 8.

FIG. 7 illustrates the end of the course of the patch 2, against a stop 12, before it is lowered. This is made possible since the ends of tracks 8 comprise at least one recess 18 in which at least one lug 6 may be housed along a direction oblique in relation to the surface of the skin, the angle thus formed by said lugs 6 is substantially equivalent to the angle of rotation produced by the patch 2 to adhere to the skin.

FIG. 8 shows patch 2 in its final position.

FIG. 9 illustrates the contact zone of patch 2 with the infusion set 1, ready to receive a pump.

FIG. 10 shows a pump 9 mounted to patch 2.

FIG. 11 also illustrates a magnet 15 disposed on the set 1 and a Hall effect detector 16 mounted to the pump, these two elements being positioned so as to verify the status of the connection between pump 9 and infusion set 1. Any other embodiment of this connection detection system may be contemplated. The magnet may, for example, be mounted to the pump 9 and the detector to the infusion set 1, or even to patch 2.

The assembly according to the invention ensures that patch 2 is correctly positioned on infusion set 1, without risk of inadvertently sticking patch 2 onto the skin of the patient. The final placement of patch 2 onto the skin may only be obtained by rotation of the patch 2 along an axis, the direction of which is defined by the lugs 6 only when the latter are housed in recesses 18. As it turns out, patch 2 is secured to the infusion set 1 with an angle ensuring a correct position of pump 9 to be connected subsequently to the infusion set 1 by means of patch 2.

The present invention offers, in particular, the following advantages:

- The lugs/tracks guiding attaches the patch to the infusion set even if the patch does not have adhesive at the surface close to the set. The curvature of the infusion site no longer plays a role in guaranteeing a correct pump/set connection.
- The patch and the infusion set are integral when they are perfectly fitted but, given that a zone of the patch lacks adhesive, they may easily be disconnected. Their locking is thus mechanically reversible.
- If one of the two elements is damaged during installation, only one part of the assembly has to be changed, not the entire assembly.
- The patch is solidly fixed to the infusion set thanks to the lugs and to the skin of the patient thanks to the adhesive.
- False positives are excluded. The patient cannot be found in a scenario where he thinks he has correctly placed his patch when this is not the case. In fact, the lugs 6 and tracks 8 pair forces the user to position the patch perfectly with relation to the infusion set. Any error is impossible since, if the assembly is poorly positioned, then the patch cannot be pulled down onto the skin and the pump cannot be installed on the patch.
- The utilization of a subassembly of two pieces in which the precision of positioning one with relation to the other is sufficient to plan to detect, with the pump, only the presence of the patch and therefore not necessarily the presence of the infusion set.
- Great ease of handling:
  - Installation in only three simple steps: Positioning of the infusion set; Installation of the patch; Connection of the pump onto the patch.
  - Removal is just as simple and pain-free. After disconnection of the pump and patch, two possibilities: removal of the assembly; Or removal in two steps by removing the patch and then the infusion set.
  - The infusion set is smaller and thus easier to install.
  - The patch comprises a gripping zone, also facilitating its installation.
- The upper faces of the base of the infusion set and of the patch base are shaped so as to facilitate installation of the pump onto the assembly.
- The patch cannot be accidentally stuck to the skin of the patient prematurely before having reached its final position with relation to the infusion set.
- The possibility of using a simplified inserter, for example without a particular reference device with relation to the patch. Only an indication of the orientation of the infusion set may be desirable so that the patient knows in which direction the patch will be oriented.
- The patch is not limited to an adhesive function. It is a support that enables the pump to be integral with the infusion set. In addition, the pump may be easily connected to and disconnected from the assembly.

The act of positioning the infusion set and then the patch is important since insertion of the infusion set is easier and does not require sophisticated insertion equipment that is costly to the patient and reduces the potential size of the insertion means. In addition, the patch disposes two security elements, the lugs that guarantee proper coupling of the assembly and the magnet that guarantees proper connection to the pump. Devices from the prior art are more complex, necessarily requiring expensive, complex and bulky insertion equipment. Such devices do not dispose security elements guaranteeing to the patient the proper installation of the assembly and the proper connection of the pump. Therefore, without these security elements, the patient may believe that he has correctly installed his pump but in reality the pump may not infuse into the patient, generating serious complications. Our device thus prevents these problems in particular thanks to the lugs and guiding tracks.

The invention claimed is:

1. An assembly adapted to secure a pumping device onto a skin of a patient, the assembly comprising:
    an infusion set configured to establish a fluid path between the patient and the pumping device;
    a patch for securing the pumping device, the patch includes an upper face configured to removably receive the pumping device, and a lower face having an adhesive portion for adhering to the skin of the patient; and
    patch-guiding elements and sliding elements, the sliding elements are configured to slide along the patch-guiding elements such that the patch mechanically couples and slides relative to the infusion set,
    wherein the patch-guiding elements and the sliding elements are further configured such that the patch mechanically couples to the infusion set and the patch can be pivoted onto the skin of the patient at a defined position relative to the infusion set, and
    wherein the patch-guiding elements comprise tracks and the sliding elements comprise lugs.

2. The assembly according to claim 1 wherein the lower face of the patch further includes a non-adhesive portion.

3. The assembly according to claim 1 wherein said infusion set includes at least one of a flexible cannula, a needle, and a microneedle.

4. The assembly according to claim 1 wherein said infusion set comprises an adhesive portion.

5. The assembly according to claim 1 wherein the patch further includes a non-adhesive portion, the non-adhesive portion of the patch comprises the sliding elements.

6. The assembly according to claim 1 wherein said infusion set comprises stop elements disposed towards one end of the patch-guiding elements and adapted to block a displacement of the sliding elements.

7. The assembly according to claim 1 wherein the sliding elements are disposed towards an edge of the patch.

8. The assembly according to claim 1 wherein the sliding elements are disposed along an axis around which the patch is configured to pivot relative to the infusion set when the sliding elements are found at a stop in the patch-guiding elements.

9. The assembly according to claim 1 wherein when the sliding elements are inserted into the patch-guiding elements, only after the sliding elements are located in a recess defining an end of the patch-guiding elements, the patch is pivotable relative to the infusion set.

10. The assembly according to claim 9 wherein the sliding elements are oriented along a direction that is parallel to a lower surface of the infusion set.

11. The assembly according to claim 1 wherein a cross section of each of said lugs is presented in a form of a rectangle bordered by two half-disks.

12. The assembly according to claim 1 further comprising a lug disposed on each side of a flared portion of the patch.

13. The assembly according to claim 1 wherein the patch-guiding elements are configured to block the patch in a defined position relative to the infusion set.

14. The assembly according to claim 1 wherein an edge of the patch comprises at least two removal zones intended to receive a finger of a user.

15. A utilization of an assembly according to claim 1 comprising the following steps:
- placing the infusion set on the skin of the patient,
- removing an adhesive film from the patch,
- putting the sliding elements in contact with the patch-guiding elements and displacing the patch along a direction that is parallel to a surface of the skin of the patient, and
- lowering the patch and putting the patch in contact with the skin of the patient.

16. The assembly according to claim 1, wherein at a first position, the patch-guiding elements and sliding elements are configured to permit a sliding movement of the patch relative to the infusion set, and at a second position, the patch-guiding elements and sliding elements are configured to permit a turning movement of the patch relative to the infusion set, and after engaging in the turning movement a blocking of the sliding movement, to place the patch on a skin of a user by the turning movement.

17. An assembly adapted to secure a pumping device onto a skin of a patient, the assembly comprising:
- an infusion set configured to establish a fluid path between the patient and the pumping device;
- a patch for securing the pumping device, the patch includes an upper face configured to removably receive the pumping device, and a lower face having an adhesive portion for adhering to the skin of the patient; and
- patch-guiding elements and sliding elements, wherein the sliding elements are configured to slide along the patch-guiding elements such that the patch mechanically couples and slides relative to the infusion set,
- wherein the patch-guiding elements and the sliding elements are further configured such that the patch mechanically couples to the infusion set and the patch can be pivoted onto the skin of the patient at a defined position relative to the infusion set, and
- wherein the patch further includes a non-adhesive portion and the non-adhesive portion includes the sliding elements.

18. An assembly adapted to secure a pumping device onto a skin of a patient, the assembly comprising:
- an infusion set configured to establish a fluid path between the patient and the pumping device;
- a patch for securing the pumping device, the patch includes an upper face configured to removably receive the pumping device, and a lower face having an adhesive portion for adhering to the skin of the patient; and
- patch-guiding elements and sliding elements, wherein the sliding elements are configured to slide along the patch-guiding elements such that the patch mechanically couples and slides relative to the infusion set,
- wherein the patch-guiding elements and the sliding elements are further configured such that the patch mechanically couples to the infusion set and the patch can be pivoted onto the skin of the patient at a defined position relative to the infusion set, and
- wherein at a first position, the patch-guiding elements and sliding elements are configured to permit a sliding movement of the patch relative to the infusion set, and at a second position, the patch-guiding elements and sliding elements are configured to permit a turning movement of the patch relative to the infusion set, and after engaging in the turning movement a blocking of the sliding movement, to place the patch on a skin of a user by the turning movement.

* * * * *